(12) United States Patent
Radstake (10) Patent No.: US 8,920,802 B2
(45) Date of Patent: Dec. 30, 2014

(54) METHODS FOR THE TREATMENT OR PREVENTION OF SYSTEMIC SCLEROSIS

(71) Applicant: Stichting Katholieke Universiteit, Nijmegen (NL)

(72) Inventor: Timothy Ruben Dirk Jan Radstake, Nijmegen (NL)

(73) Assignee: Stichting Katholieke Universiteit, Nijmegen (NL)

( * ) Notice: Subject to any disclaimer, the term of this patent is extended or adjusted under 35 U.S.C. 154(b) by 0 days.

(21) Appl. No.: 13/928,557

(22) Filed: Jun. 27, 2013

(65) Prior Publication Data

US 2013/0287794 A1    Oct. 31, 2013

Related U.S. Application Data

(63) Continuation of application No. 13/138,608, filed on Sep. 8, 2011, now Pat. No. 8,486,407.

(30) Foreign Application Priority Data

Mar. 8, 2009   (EP) .................................... 09154582
Mar. 8, 2010   (WO) ................. PCT/EP2010/052919

(51) Int. Cl.
*A61K 39/00*      (2006.01)
*A61K 39/395*     (2006.01)
*A61K 38/17*      (2006.01)

(52) U.S. Cl.
CPC ............. *A61K 39/3955* (2013.01); *A61K 38/17* (2013.01); *A61K 39/39541* (2013.01)
USPC .................. 424/140.1; 424/130.1; 424/172.1; 424/158.1

(58) Field of Classification Search
CPC .................. A61K 2039/505; A61K 2035/122; A61K 47/48561; A61K 51/1027; A61K 2300/00; A61K 39/00; A61K 39/3955; A61K 2039/6056; A61K 35/15; A61K 39/0008; A61K 2039/57; A61K 35/17; A61K 39/395; A61K 39/008; G01N 33/564; G01N 33/5047
See application file for complete search history.

(56) References Cited

U.S. PATENT DOCUMENTS

| 6,312,694 | B1 | 11/2001 | Thorpe et al. | |
| 8,034,905 | B2 | 10/2011 | Kavlie et al. | |
| 8,535,669 | B2 * | 9/2013 | Vairo et al. | 424/133.1 |
| 2009/0041753 | A1 | 2/2009 | Miller et al. | |

FOREIGN PATENT DOCUMENTS

| WO | WO 95/00543 | 1/1995 |
| WO | WO 02/074914 | 9/2002 |
| WO | WO 2006/125077 | 11/2006 |
| WO | WO 2007/062175 | 5/2007 |
| WO | WO 2010/102983 | 9/2010 |

OTHER PUBLICATIONS

Hinchcliff et al. 2008. Am Fam. Phys 78:961-968.*
Kafaja et al. 2013. Journal of Immunl. 190 Abstract 43.28, p. 3133.*
Van Bon et al, 2014. NEJM 370:433-43.*
Korn, et al. Iloprost Reduces Procoagulant Activity in the Extracorporeal Circuit; Journal of Surgical Research 55, 433-440 (1993).
Kowal-Bielecka et al.; β Thromboglobulin and platelet factor 4 in bronchoalveolar lavage fluid of patients with systemic sclerosis; Ann Rheum Dis 2005; 64; 484-486.
Lakos, et al. Increased Bleomycin-Induced Skin Fibrosis in Mice Lacking the Th1-Specific Transcription Factor T-bet; Pathobiology 2006; 73: 224-237.
Mueller, et al. CXCL4-induced migration of activated T lymphocytes is medicated by the chemokine receptor CXCR3; Journal of Leukocyte Biology, vol. 83, Apr. 2008.
PCT Written Opinion and Search Report of PCT/EP2010/052919 dated Aug. 31, 2010.
Piludu, et al; Bosentan treatment in pulmonary arterial hypertension secondary to systems sclerosis; Allergy 63 (Suppl. 88) 2008; p. 353.
Romagnani, et al.; CXCR3-mediated opposite effects of CXCL10 and CXCL4 on TH1 or TH2 cytokine production; J. Allergy Clin. Immunology, vol. 116, No. 6; 2005 pp. 1372-1379.
PCT International Preliminary Report on Patentability and Written Opinion, PCT/EP2010/052919, dated Sep. 13, 2011.
Pervushina et al., 2004, J. Immunology, pp. 2060-2067, vol. 173.
Pope et al., Arthritis and Rheum, pp. 1351-1358, vol. 44.

* cited by examiner

*Primary Examiner* — Shulamith H Shafer
(74) *Attorney, Agent, or Firm* — TraskBritt, P.C.

(57) ABSTRACT

The invention is in the field of molecular immunology, more in particular, in the field of the prevention or treatment of autoimmune diseases, more in particular, systemic sclerosis or scleroderma. The invention is based on the observation that SSC patients have an elevated plasma level of CXCL4. This was found to contribute to the pathogenesis of SSc, in particular, fibrosis. When CXCL4 was neutralized in in vitro experiments, the fibrotic effects could be neutralized. This led us to conclude that SSc may be cured by reducing the plasma level of CXCL4. The invention, therefore, relates to a method for treatment or prevention of fibrosis in patients with scleroderma, wherein the plasma level of CXCL4 is reduced.

6 Claims, 7 Drawing Sheets

METHODS FOR THE TREATMENT OR PREVENTION OF SYSTEMIC SCLEROSIS

CROSS-REFERENCE TO RELATED APPLICATIONS

This is a continuation of U.S. patent application Ser. No. 13/138,608, filed Sep. 8, 2011, pending, which application is a national phase entry under 35 U.S.C. §371 of international Patent Application PCT/EP2010/052919, filed Mar. 8, 2010, published in English as International Patent Publication WO 2010/102983 A1 on Sep. 16, 2010, which claims the benefit under Article 8 of the Patent Cooperation Treaty to European Patent Application Serial No. 09154582.2, filed Mar. 8, 2009.

TECHNICAL FIELD

The invention is in the field of molecular immunology, more in particular, in the field of the prevention or treatment of autoimmune diseases, more in particular, systemic sclerosis or scleroderma.

BACKGROUND

Scleroderma or Systemic Sclerosis (SSc) is an autoimmune connective tissue disorder of unknown cause characterized by microvascular injury, excessive fibrosis of the skin, and distinctive visceral involvement including the heart, lung, kidneys and gastrointestinal tract. Scleroderma is a progressive condition in which fibrous tissue grows abnormally, causing the skin to thicken and harden, often disfiguring and disabling patients. It affects between 5,000-10,000 new persons annually (USA) and is associated with a high morbidity and a poor prognosis. Overall, scleroderma affects an estimated 300,000 Americans, most of them women.

Forty percent of all scleroderma patients develop at least moderate restrictive lung disease. A high proportion of scleroderma patients (80 percent) develop lung involvement, either interstitial lung disease and/or pulmonary hypertension, which are the leading causes of death due to scleroderma. The mortality rate in scleroderma patients with severe restrictive lung disease is about 30 percent within 10 years of onset.

The statistics underscore the need for effective treatment, preferably at an early stage in the illness, to prevent progression to severe interstitial lung disease. SSc is treated with oral medications to halt the progression of disease. These drugs include cyclophosphamide, high-dose prednisolone or even stem cell transplantation, all having severe side effects. In SSc, drugs that improve circulation, promote gastrointestinal function, preserve kidney function, and control high blood pressure are also given. Cyclophosphamide is an anti-cancer drug that suppresses the immune system. This is the first drug that has been proven to alleviate the most devastating effects of SSc. Patients taking cyclophosphamide had a significant improvement in lung function and a reduction in breathlessness.

Although many research groups work on the unraveling of SSc pathogenesis, to date, the exact pathways underlying the pathogenesis of SSc remain unknown. Currently, most of the research is focused on the underlying pathways that cause fibroblast activation. A deregulated growth and activation of fibroblasts has often suggested to be implicated in SSc. However, a mode of action that is responsible for this ongoing activation of fibroblasts has not been identified.

DISCLOSURE

The invention is based on the observation that SSC patients have an elevated plasma level of CXCL4. This was found to contribute to the pathogenesis of SSc, in particular, fibrosis. When CXCL4 was neutralized in in vitro experiments, the fibrotic effects could be neutralized. This led us to conclude that SSc may be cured by reducing the plasma level of CXCL4. The invention, therefore, relates to a method for treatment or prevention of fibrosis in patients with scleroderma, wherein the plasma level of CXCL4 is reduced.

It was also found that CXCL4 was produced by pDCs in the blood circulation of patients with SSc. A method as described above is, therefore, preferably performed by depleting pDCs from the circulation of a patient with scleroderma.

BRIEF DESCRIPTION OF THE DRAWINGS

FIG. 1: Increased frequency of plasmacytoid DCs in SSc patients. Using the DC enumeration kit (Miltenyi Biotec), SSc patients showed a clearly increased frequency of plasmacytoid DCs (pDCs, BDCA2+), whereas the frequency of myeloid DCs (mDCs, BDCA1+ or BDCA3+) was similarly distributed among groups. Patients with diffuse cutaneous SSc especially had a markedly raised frequency of pDCs that was most marked in those having a disease duration shorter than 2 years.

FIG. 2: The increased frequency of pDCs is most pronounced in diffuse SSc. Using magnetic bead isolation of pDCs (BDCA4+ cells), it is clear that patients with diffuse cutaneous SSc have a significantly increased frequency of pDCs compared to those having the limited cutaneous phenotype. In turn, patients having early diffuse (<2 years of disease duration) SSc have significantly higher frequencies of circulating pDCs than those with late diffuse disease (>3 years of disease duration).

FIG. 4: CXCL4 directly stimulates fibroblasts. Although unstimulated skin fibroblasts do not express high levels of COMP, co-incubation with SSc plasma resulted in a clear up-regulation of COMP expression that was abrogated by heparinase, a natural CXCL4 antagonist. In contrast, plasma from healthy controls did not induce the up-regulation of COMP.

DETAILED DESCRIPTION

Figure 1:
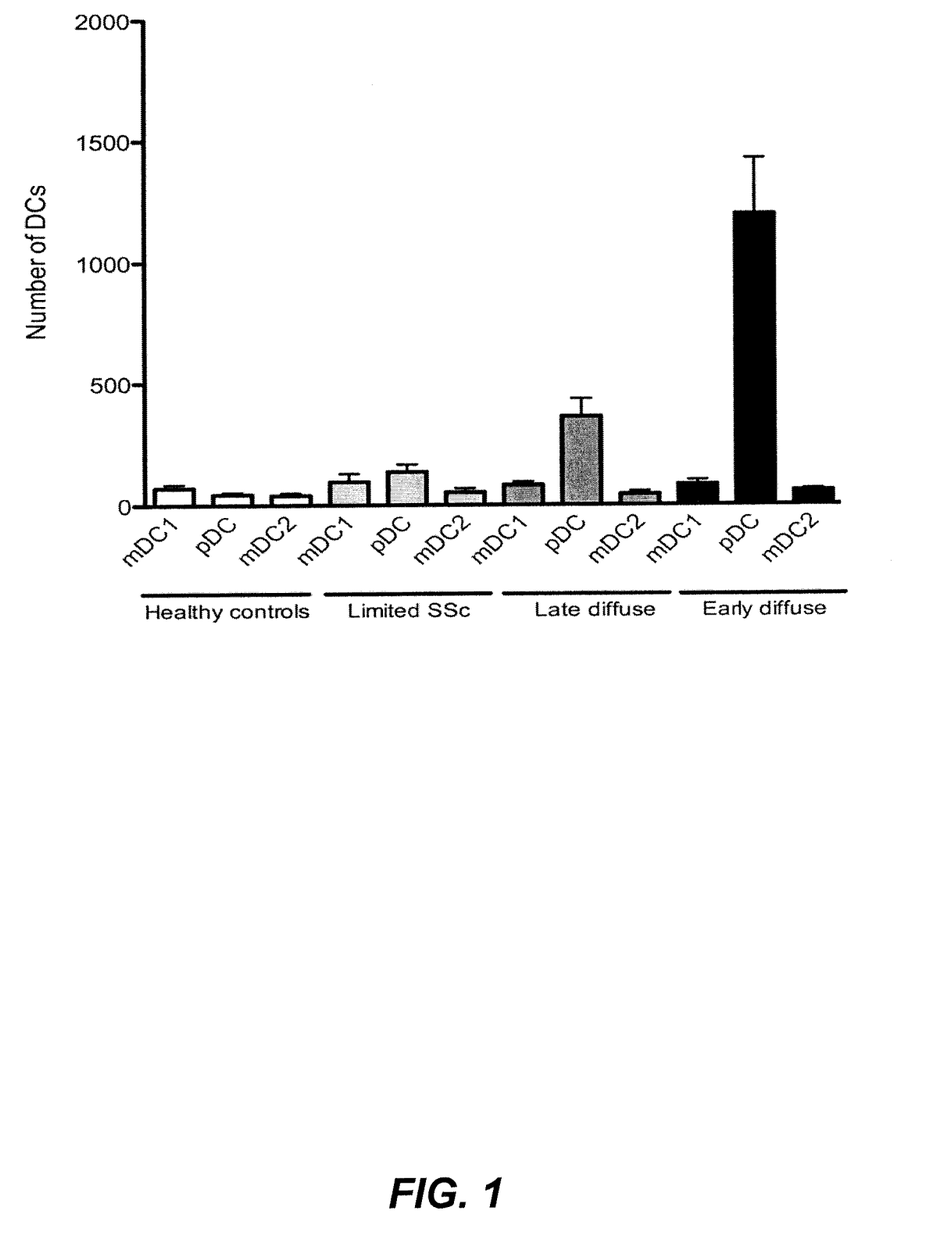
Figure 2:
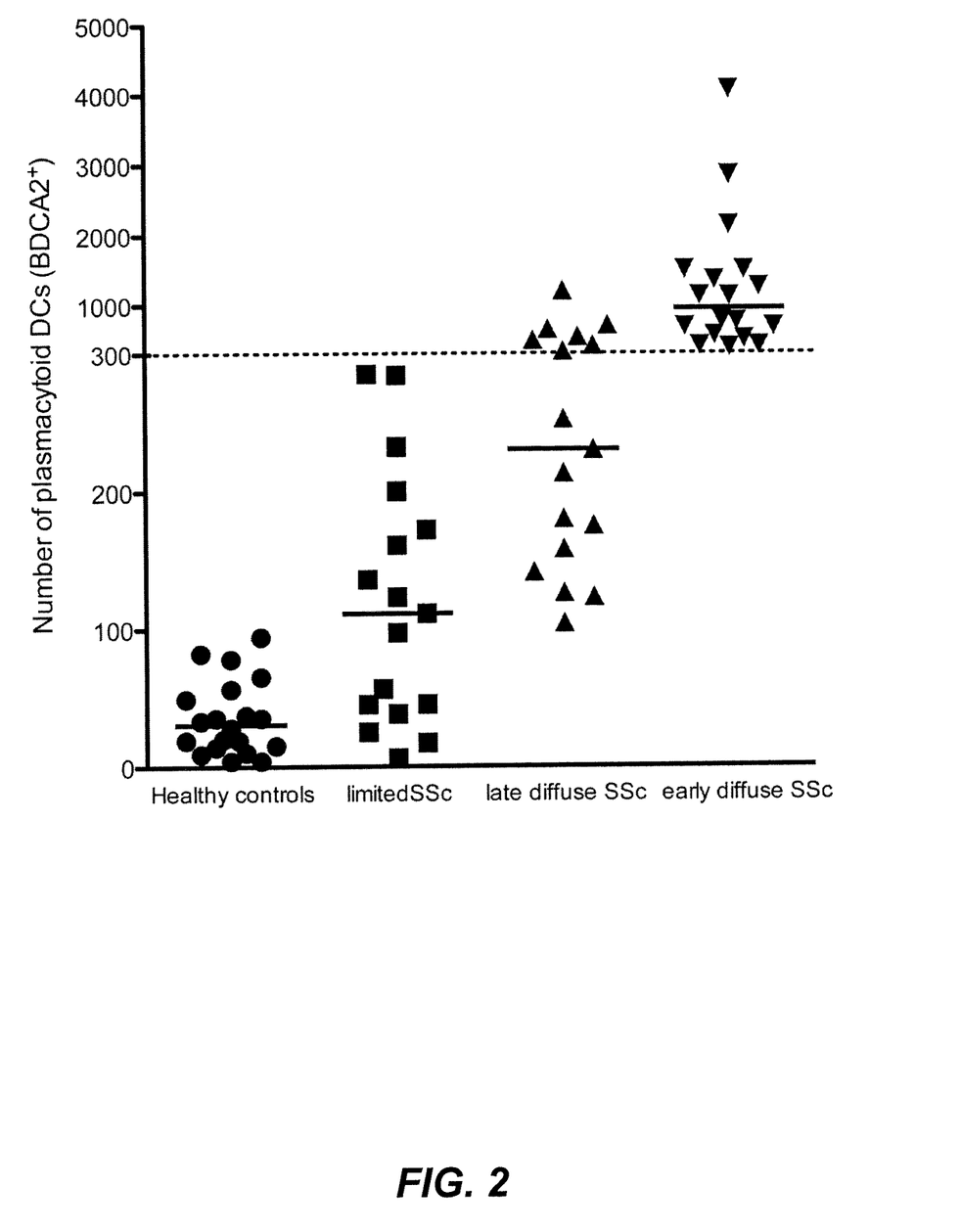

It was found that the frequency of plasmacytoid DCs (pDCs) is markedly increased in SSc patients. This is illustrated in FIG. 1. In particular, the frequency of pDCs was increased in patients with the diffuse cutaneous subtype of SSc. The frequency of pDCs was highest in patients suffering from early diffuse SSc. The number of pDCs in individual SSc patients, as compared to normal healthy controls, is shown in FIG. 2.

It was also found that plasma from SSc patients contains high levels of CXCL4. CXCL4 is a chemokine described to bind to CXCR3, more specifically, the splice variant CXC3b, which is in contrast to CXLC9, CXCL10 and CXCL11 that bind to CXCR3a (Lasagni et al., *J Experimental Medicine* 2003). CXCL4 is known to induce apoptosis in endothelial cells leading to endothelial cell death. In addition, CXCL4 is known to have potent anti-angiogenic properties and known to induce fibroblast activation via activation of monocyte-derived dendritic cells.

Figure 3:
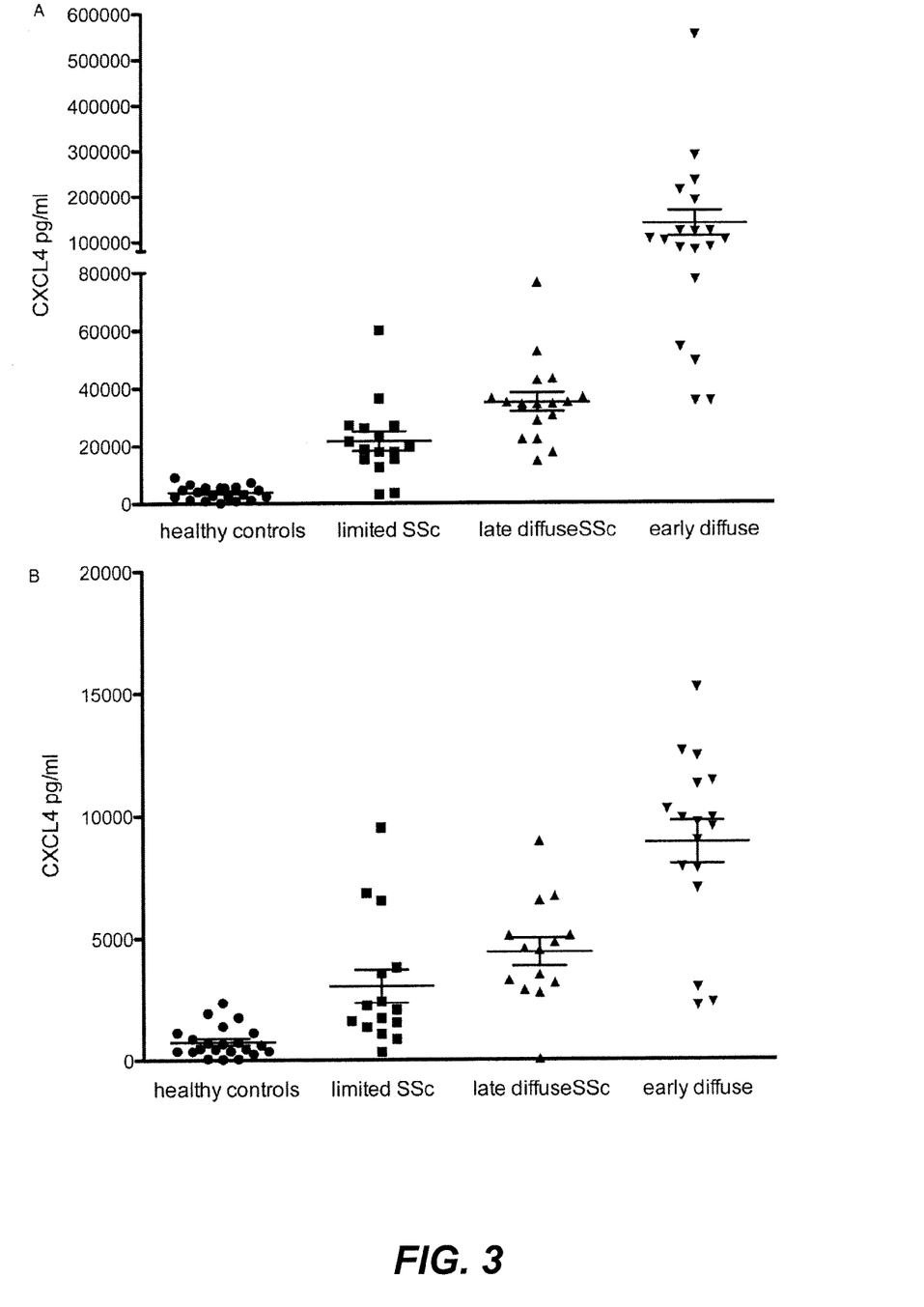
FIG. 3: CXCL4 in pDC supernatant and plasma from SSc patients is markedly increased. CXCL4 levels were measured using ELISA techniques in pDC supernatant (Panel A) derived from healthy controls and patients with limited, late diffuse and early diffuse SSc. CXCL4 levels are increased in all SSc patients but more pronounced in patients having diffuse SSc, especially those having early diffuse cutaneous SSc. Panel B displays the CXCL4 levels in the plasma of healthy controls and SSc patients. CXCL4 levels in both pDC supernatant as well as plasma closely reflect the frequency of pDCs in the circulation.

CXCL4 was measured in a standard ELISA assay and the results are illustrated in FIG. 3, Panel A. It is shown that CXCL4 was overproduced by pDCs of SSc patients since elevated levels of CXCL4 could also be detected in the supernatant of pDCs isolated from early diffuse SSc patients. This is illustrated in FIG. 3, Panel B. It was noted that the production of CXCL4 in pDC supernatant closely mirrored the frequency of pDCs in plasma. Since CXCL4 was originally identified as a sole platelet activation marker, the possibility was excluded that platelets contaminated the pDCs supernatants by measuring the β-TG content, which was negligible.

Hence, it was concluded that CXCL4 is over-produced by pDCs in patients with SSc. This was confirmed in a whole proteome analysis using SELDI-TOF. Analysis of pDC revealed that SSc pDCs were solely committed to produce a few proteins that could be identified as CXCL4 or CXCL4-precursor molecules.

Figure 4:
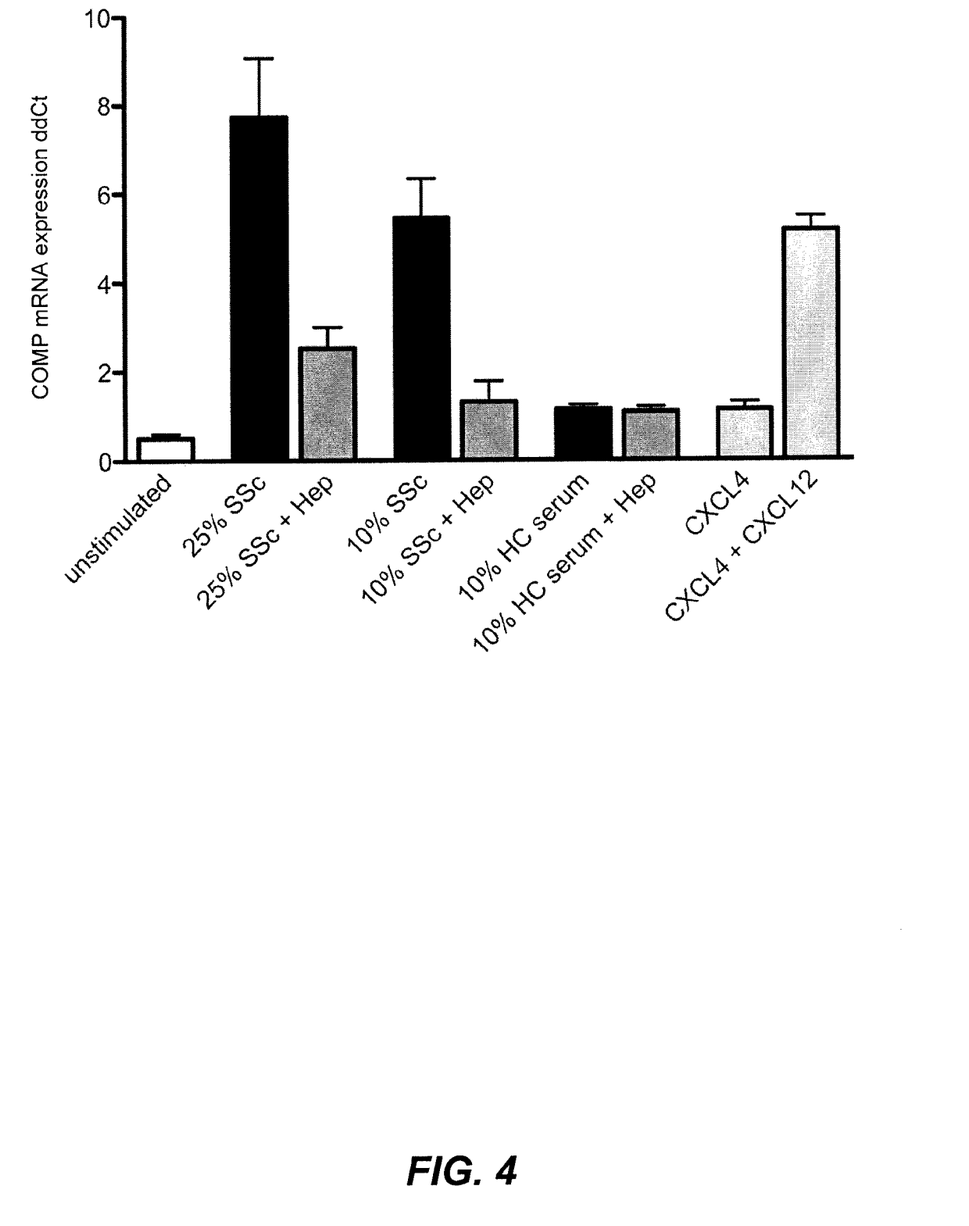

It was also shown that CXCL4 plays a role in fibroblast activation in SSc patients. To that end, the expression of known fibroblast activation markers TGFβR, COMP and αSMA in healthy fibroblasts co-incubated with SSc plasma was measured. It was found that SSc plasma induced the expression of these markers for fibroblast activation significantly and in a dose-dependent manner (FIG. 4). In addition, the plasma from healthy donors had no effect and the effect of SSc plasma was abrogated using heparinase, a natural antagonist of CXCL4. We conclude that an elevated level of pDCs in Ssc patients contributes to the fibrotic process.

Figure 5:
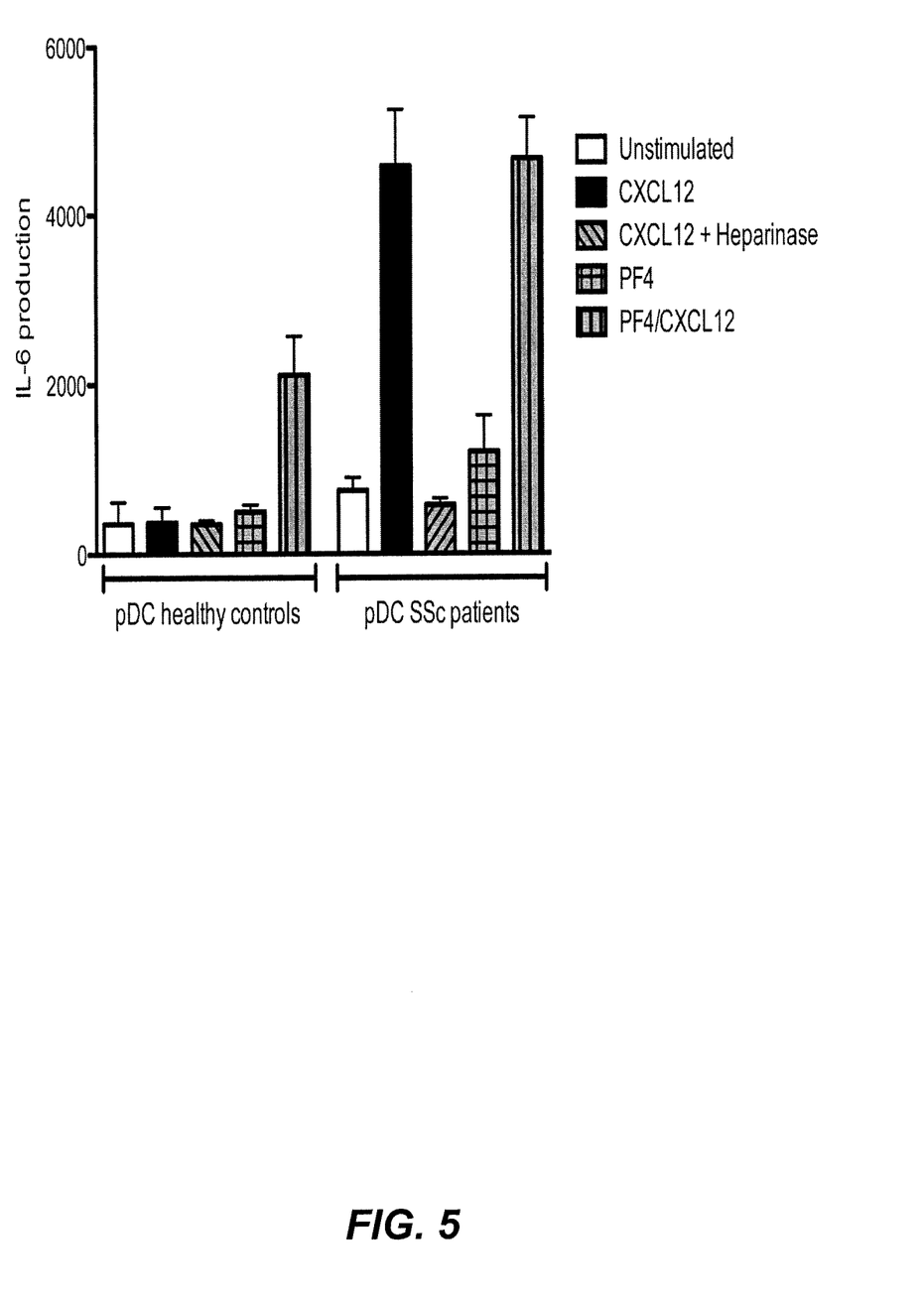
FIG. 5: The addition of CXCL12 to SSc pDCs induces a self-perpetuating activation loop. Although the IL-6 production by pDCs from healthy controls could only be induced by the co-incubation with CXCL4+CXCL12, SSc pDCs produced large amounts of IL-6 upon the addition of CXCL12. This effect could be fully abrogated by the addition of heparinase underscoring the CXCL4 dependency in this system. The addition of CXCL4 only did not have a significant effect, suggesting the need for CXCL12 in the CXCL4-dependent pDC activation loop.
Figure 6:
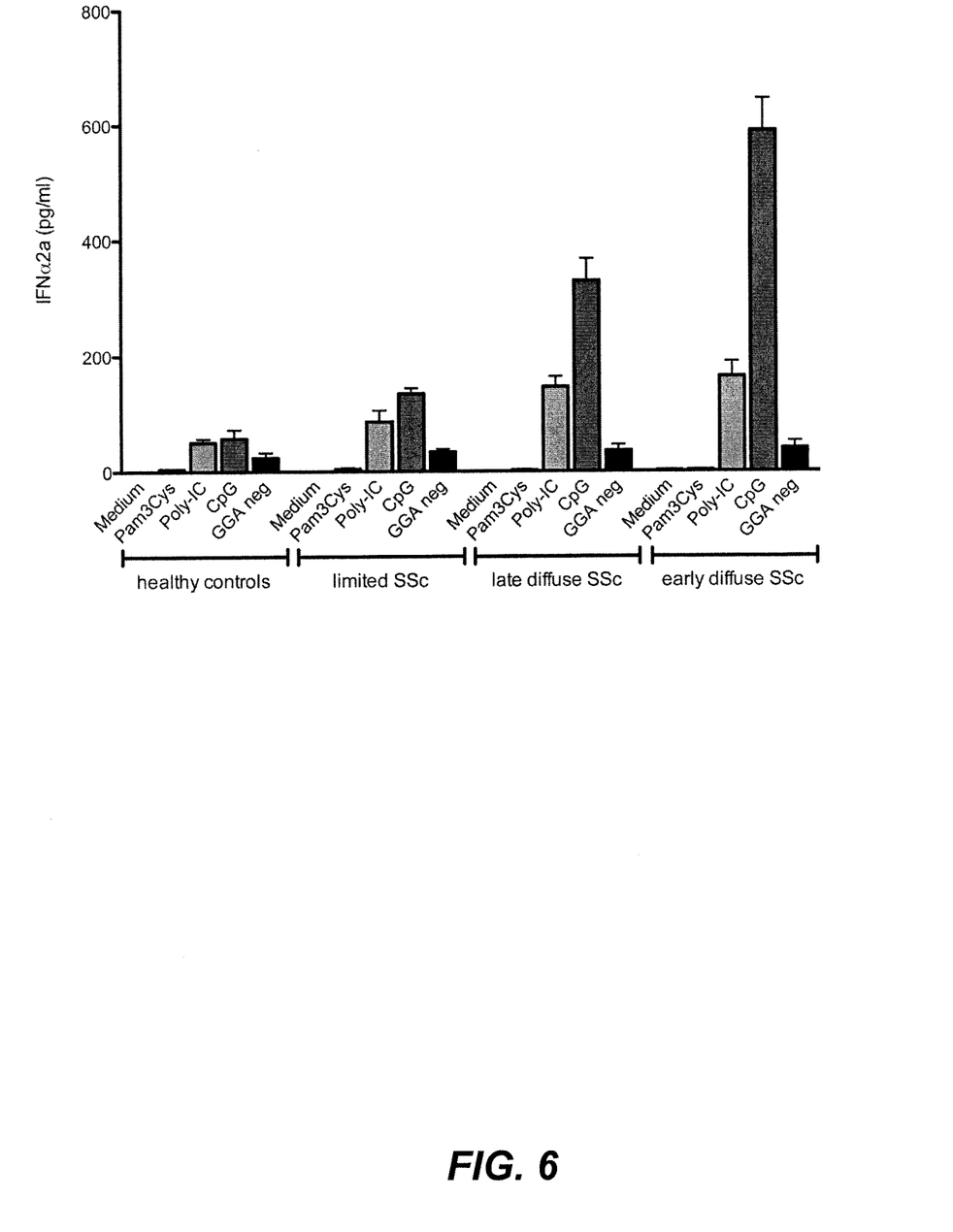
FIG. 6: pDCs from SSc patients secrete higher levels of Type I IFNs upon TLR-mediated stimulation. Upon stimulation of pDCs with ligands for TLR2, TLR3, TLR4 and TLR9, pDCs from SSc patients produce significantly more type I IFN compared with healthy controls. More specifically, SSc patients with diffuse cutaneous disease showed a markedly increased secretion of type I IFN.

CXCL4 on its own was found to be unable to stimulate pDCs to produce pro-inflammatory molecules; neither pDCs from normal individuals nor pDCs from SSc patients produced pro-inflammatory molecules. Only in the presence of CXCL12-specific stimulation of pDCs derived from SSc patients could be observed. This is illustrated in FIG. 6. Therein, the production of pro-inflammatory molecules was measured in the presence of pDCs from healthy individuals as compared to pDCs isolated from SSc patients.

pDCs from healthy controls were incubated with plasma from SSc patients and healthy controls, after which the production of pro-inflammatory molecules was measured. The addition of plasma from SSc patients and healthy controls had no effect. pDCs from healthy individuals were incubated, as well as from SSc patients with SSc plasma and healthy control plasma, with and without the presence of CXCL12. It was found that only the combination of SSc plasma and CXCL12 led to a significantly increased level of IL-6 and IL-12. To assure that this effect was due to the "auto-activation" of pDCs by endogenous CXCL4, CXCL4 was added to the cultures of pDCs from healthy individuals with healthy control serum and CXCL12. The addition of CXCL4 to these experiments induced IL-6 and IL-12 secretion to the same levels as the combination of SSc plasma and CXCL12 (FIG. 5). In addition, the addition of heparinase fully abrogated the effect of SSc plasma and CXCL12 on pDCs.

Without wanting to be bound by theory, it was hypothesized that CXCL12 (also known as SDF-1) binds to CXCR4, thereby initiating chemo-attractive properties aimed at the recruitment of pDC toward the site of inflammation. CXCL12 is known to be highly presented in the skin of SSc patients and likely to be produced by local fibroblasts. In support of this hypothesis, it is mentioned that monocyte-derived DCs were found to be insensitive to CXCL4 unless CXCL12 is present. It is currently unknown how CXCL12 sensitizes DCs to the effect of CXCL4 (Cipriani et al., *Arthritis Rheum.* 2006 September, 54 (9):3022-33).

It is known that pDCs are stimulated mostly via toll-like receptor 9 (TLR9), via which they mainly make type I interferons (IFNs). As such, pDCs are considered the main producers of this cytokine.

Challenged by the question "what induces the increased CXCL4 production by pDCs," the role of toll-like receptors (TLR) was investigated. These experiments showed that TLR3-, TLR7/8- and TLR9-mediated stimulation induced CXCL4 secretion by pDCs. Interestingly, DCs from SSc patients were found to produce much more IFNs and IL6 than those from healthy controls (FIG. 6). A clearly increased secretion of IFNα in IdSSc patients, IdSSc patients and edSSc patients was observed.

Figure 7:
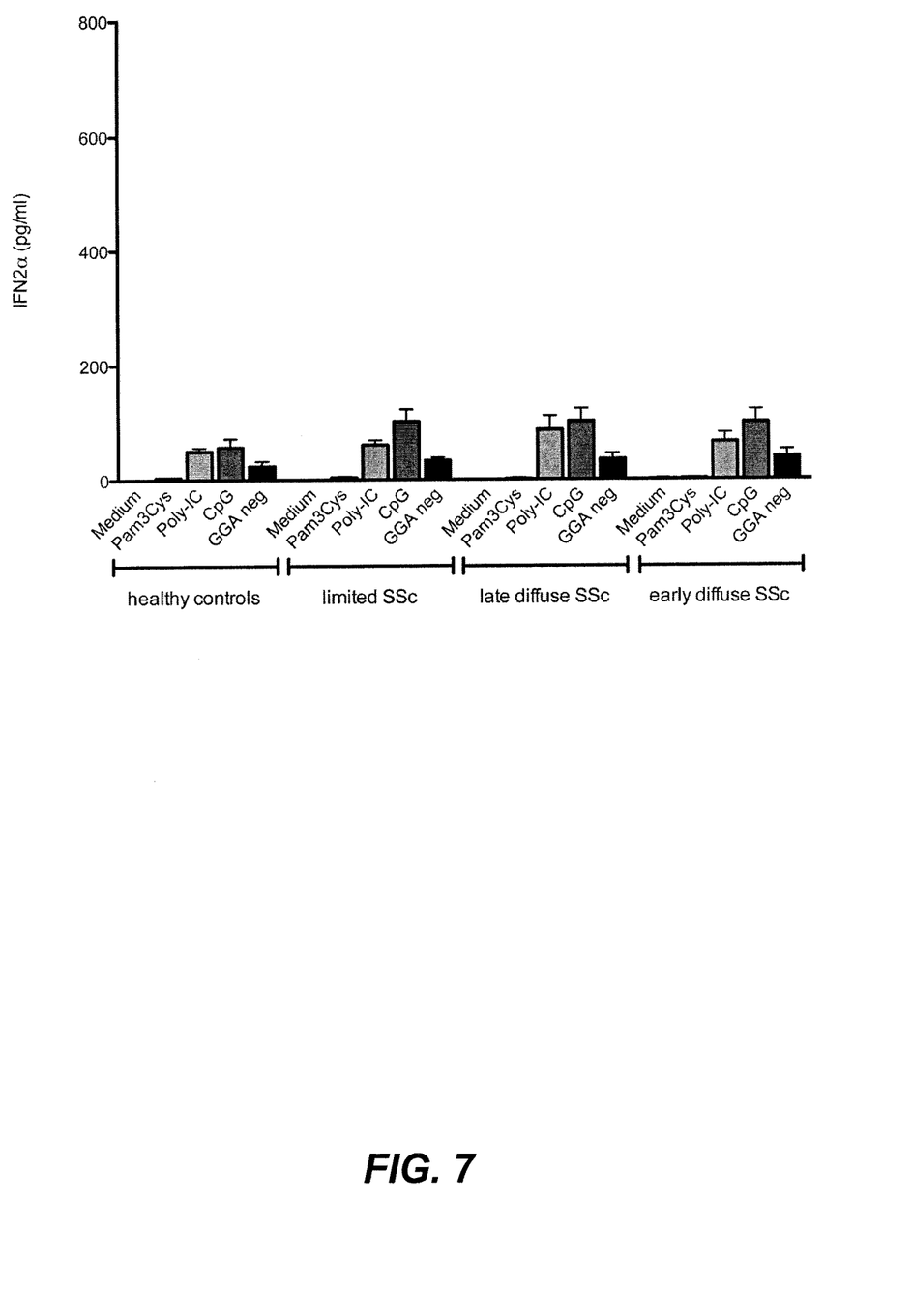
FIG. 7: The augmented TLR response by pDC in SSc is abrogated by neutralization of PF4. The administration of heparinase, a natural CXCL4 antagonist, fully abrogates the augmented TLR response as observed in SSc patients.

This shows that the potentiated TLR response by pDCs is caused by a CXCL4-dependent TLR augmentation. In support of this, neutralization of CXCL4 led to a full abrogation of this TLR augmentation, showing that CXL4 underlies this phenomenon (FIG. 7).

To further substantiate these findings, pDCs from healthy controls were incubated with CXCL12, CXCL4 or its combination dose dependently. These experiments demonstrated that CXCL4 in combination with CXCL12 led to an augmentation of the TLR response.

In conclusion, these observations show that CXCL4 (in conjunction with CXCL12) plays a central role in the pathogenesis of SSc. The mechanism for that is auto-activation of pDCs resulting in a potentiated TLR response and further CXCL4 production.

Patients with SSc may, therefore, benefit from methods that remove CXCL4 and/or pDCs, for instance, from the blood circulation. That may be accomplished in a number of ways, which are known in the art per se.

Patients with scleroderma may benefit from a treatment wherein the effects of the CXCL4 produced in excess are neutralized or counteracted, for instance, by removing CXCL4 from circulation. In the alternative, CXCL4 may be prevented from binding to its receptor. The invention, therefore, relates to a compound capable of binding to CXCL4 for use in the treatment or prevention of fibrosis in patients with scleroderma.

Compounds capable of binding to CXCL4 may be compounds capable of binding to CXCL4 under physiological conditions.

Compounds capable of binding to CXCL4 per se are known in the art. For instance, fragments of the receptor or fragments of CXCL4 will be suitable compounds. In a preferred embodiment, specific antibodies may be employed in order to remove CXCL4, for instance, from the circulation. This may be accomplished by plasmapheresis.

Antibodies against CXCL4 are available in the art. They have been described, for instance, in Vandercapellen et al., *J. Leukocyte Biol.* 82, 1519 (2007), and are commercially available from R&D Systems, 614 McKinley Place NE, Minneapolis Minn. 55413.

Given the teachings of the present disclosure, it will be within the routine skills of a person skilled in the art to design and develop materials and methods for removing or counteracting the effects of CXCL4 and/or DCs such that patients with SSc may benefit from these materials and methods.

For that purpose, CXCL4 antagonists may be advantageously employed. Antagonists for CXCL4 are known to the skilled person. As an example, heparinase is disclosed and exemplified herein.

In another embodiment, the invention also relates to a compound capable of interfering with the in vivo production of CXCL4 for treatment or prevention of fibrosis in patients with scleroderma. Compounds capable of interfering with the in vivo production of CXCL4 per se are known in the art. The invention, therefore, also relates to a method for treatment or prevention of fibrosis in patients with scleroderma by interfering with the in vivo production of CXCL4. Such methods may encompass interference at the level of transcription or translation of CXCL4. Such methods are known in the art and may now advantageously be used in the treatment of scleroderma.

A reduction in the level of CXCL4 in a patient's body may be accomplished by a therapy in vivo. Alternatively, patients with SSc may also benefit from in vitro methods that reduce the level of CXCL4 in blood. Such may be done directly by applying a compound capable of binding to CXCL4 and contacting that compound with blood obtained from a patient with SSc. It may also be accomplished by reducing the number of DC that produce the CXCL4 in patients with scleroderma. This may also be accomplished in an in vitro method wherein the previously isolated blood or plasma from a patient with scleroderma is contacted with a compound or device capable of reducing or depleting the number of pDCs in solution. The invention, therefore, also relates to an in vitro method for reducing the level of CXCL4 and/or the number of pDCs in blood obtained from a patient with scleroderma. In more detail, the invention relates to an in vitro method for reducing the level of CXCL4 and/or the number of pDCs in a sample obtained from a patient with scleroderma, comprising the steps of:

a. providing the sample obtained from a patient with scleroderma
b. contacting the sample with a compound capable of binding to CXCL4
c. allowing the compound to bind to CXCL4 in order to form a complex
d. removing the complex from the sample, thereby reducing the level of CXCL4 and/or the number of pDCs.

Devices capable of reducing the level of CXCL4 and/or pDCs in blood are known in the art. Preferably, CXCL4 and/or pDCs are removed from circulation, for instance, using a commercially available technique provided by Miltenyi (Jongbloed et al., *Arthritis Res. Ther.* 2006, 8 (1):R15).

Miltenyi produces and markets such a device that may be advantageously used in the new treatment according to the invention. Hence, the invention relates to a device capable of reducing the level of CXCL4 and/or pDCs in blood for the treatment or prevention of fibrosis in patients with scleroderma.

Alternatively, a method according to the invention may also comprise a step wherein the binding of CXCL4 to its receptor is blocked or otherwise prevented or down-regulated or decreased. The invention, therefore, also provides a method for treatment or prevention of fibrosis in patients with scleroderma by interfering with the binding of CXCL4 to its receptor.

EXAMPLES

Example 1

Isolation of PBMCs, Plasmacytoid DCs And Phenotypic Characterization

PBMCs were isolated from heparinized venous blood (100 ml) by using density-gradient centrifugation over Ficoll-Paque (Amersham Bioscience). Next, plasmacytoid DCs (pDCs) were isolated using the BDCA4 magnetic isolation kit from Miltenyi Biotec according to the manufacturer's protocol. All procedures were carried out on ice and after the isolation of pDCs, these cells were counted using counter-chambers and directly transferred to RPMI medium without any additions in a concentration of 1 million cells/ml. After pelleting, the supernatant was collected and stored at $-80°$ C. until further analysis. The cells were then resuspended in RPMI supplemented with 2 nM L-glutamine, 100 U/μL/ml penicillin/streptomycin (Life Technologies), and 10% FCS (BioWhitacker), after which cells were brought into culture for further analysis. Directly after isolation, a part of the BDCA4+ cells were resuspended in FACS buffer and were analyzed for the expression of BDCA1, BDCA2, BDCA3, CD80, CD86, MHC and FcγRs applying standard flow cytometry protocols. During the first experiments, the pDCs diamond kit from Miltenyi Biotec was exploited to replicate our data having so-called "untouched pDCs." In all experiments, direct DC enumeration was performed using the DC enumeration kit from Miltenyi Biotec according to the manufacturer's protocol.

Example 2

Measurement of Inflammatory Mediators

Supernatant from unstimulated pDCs was stored after 1 and 24 hours of culture. In addition, pDCs were stimulated with ligands specific for toll-like receptor 2 (TLR2, pam3Cys), TLR3 (Poly-IC), TLR4 (LPS), TLR7/TLR8 (R848) and TLR9 (CPG) for 24 hours, after which supernatant was collected. In all these supernatants, the levels of multiple inflammatory mediators (IL-8, TNF, IFNγ, IFNα, MCP-1, MIP 1β, IL-6, IL-1β, IL-12. IL-23, IL-17F, IL-17A) were measured using Luminex technology as previously described (Roelofs et al., *Arthritis Rheum.* 2005 August, 52 (8):2313-22; Roelofs et al., *Ann. Rheum. Dis.* 2009 September, 68 (9):1486-93, Epub 2008 Sep. 2; Wenink et al., *J. Immunol.* 2009 Oct. 1, 183 (7):4509-20, Epub 2009 Sep. 4). To study the full proteome in pDCs, the 1-hour spontaneous supernatants were used for analysis in the SELDI-TOF. Exploiting this technique, 40 supernatants were tested originating from healthy controls (n=10) and SSc patients having limited cutaneous (n=10), late diffuse (n=10) and early diffuse (n=10) disease as previously described (Radstake et al., PLos ONE 2009). The expression of CXCL4 and β-TG was measured by commercially available ELISAs used following the manufacturer's protocols.

Example 3

Stimulation of Plasmacytoid DCs And Investigating the Self-Perpetuating Loop

Since the literature suggests an important role for CXCL12 in the CXCL4-mediated activation of pDCs, the potential role of this loop in SSc was investigated (van der Vliet et al., *J. Experimental Medicine* 2003 Sep. 1, 198 (5):823-3). To this aim, first pDCs from healthy controls and SSc patients were co-cultured with combinations of CXCL4 and/or CXCL12. During these experiments, pDCs were cultured with RPMI only, RPMI/CXCL12, RPMI/CXCL12/CXCL4 and RPMI/CXCL12/heparinase. In addition, the effect of CXCL4 on the TLR pathways was investigated by pre-incubation of pDCs with CXCL4 or the combination CXCL4/CXCL12, after which, pDCs were consecutively stimulated with TLR ligands. After 24 hours of incubation, the production of IFNα, IL-12 and IL-6 was measured by Luminex.

Example 4

CXCL4-Mediated Activation of Fibroblasts

Skin fibroblasts were isolated from healthy skin biopsies and cultured according to standardized protocol as described previously (Farina, *Ann. Rheum. Dis.* 2009 March, 68 (3): 435-41). When confluent, fibroblasts were replated and cultured for an additional 24 hours to allow attachment to the culture plates. Subsequently, fibroblasts were incubated with combinations of plasma from healthy controls and SSc patients, plasma and heparinase and CXCL4/CXC12. After 48 hours of culture, the expression of COMP was measured by real-time PCR as previously described (Farina, *Ann. Rheum. Dis.* 2009 March, 68 (3):435-41).

What is claimed is:

1. A method for treating a subject diagnosed as suffering from diffuse cutaneous systemic sclerosis, the method comprising:
    providing a sample obtained from the subject;
    contacting the sample with a compound that binds to plasmacytoid dendritic cells;
    allowing the compound to bind to plasmacytoid dendritic cells in order to form a complex; and
    removing the complex from the sample,
    wherein the sample having the complex removed is administered to the subject.

2. The method according to claim 1, wherein the sample is blood, plasma, or serum.

3. The method according to claim 1, wherein the compound that binds to plasmacytoid dendritic cells is an antibody.

4. The method according to claim 3, wherein the antibody is specific for a plasmacytoid dendritic cell antigen.

5. The method according to claim 3, wherein the antibody is selected from the group consisting of anti-BDCA2, anti-BDCA4, and anti-CXCL4.

6. The method according to claim 1, wherein the diffuse cutaneous systemic sclerosis is early diffuse cutaneous systemic sclerosis.

* * * * *

UNITED STATES PATENT AND TRADEMARK OFFICE
CERTIFICATE OF CORRECTION

PATENT NO. : 8,920,802 B2  
APPLICATION NO. : 13/928557  
DATED : December 30, 2014  
INVENTOR(S) : Timothy Ruben Dirk Jan Radstake It is certified that error appears in the above-identified patent and that said Letters Patent is hereby corrected as shown below:

In the specification:

COLUMN 1, LINE 7, change "pending," to --now U.S. Patent No. 8,486,407, issued on July 16, 2013,--

Signed and Sealed this
Fifth Day of January, 2016

Michelle K. Lee
*Director of the United States Patent and Trademark Office*